(12) United States Patent
Shai et al.

(10) Patent No.: US 8,162,812 B2
(45) Date of Patent: Apr. 24, 2012

(54) COMBINED CRYOTHERAPY AND BRACHYTHERAPY DEVICE AND METHOD

(75) Inventors: Eyal Shai, Karkur (IL); Nir Berzak, Givataim (IL)

(73) Assignee: Icecure Medical Ltd., Caesarea (IL)

( * ) Notice: Subject to any disclaimer, the term of this patent is extended or adjusted under 35 U.S.C. 154(b) by 0 days.

(21) Appl. No.: 12/722,845

(22) Filed: Mar. 12, 2010

(65) Prior Publication Data
US 2010/0234670 A1    Sep. 16, 2010

Related U.S. Application Data

(60) Provisional application No. 61/159,497, filed on Mar. 12, 2009.

(51) Int. Cl.
*A61N 5/00* (2006.01)
(52) U.S. Cl. .................................. 600/2; 600/3
(58) Field of Classification Search ................ 600/1–8; 606/20–26
See application file for complete search history.

(56) References Cited

U.S. PATENT DOCUMENTS

| | | |
|---|---|---|
| 3,234,746 A | 2/1966 | Smith |
| 3,358,472 A | 12/1967 | Kipling |
| 3,664,344 A | 5/1972 | Bryne |
| 3,699,775 A | 10/1972 | Cowans |
| 3,712,306 A | 1/1973 | Bryne |
| 3,736,936 A | 6/1973 | Basiulis |
| 3,800,552 A | 4/1974 | Sollami |
| 3,862,630 A | 1/1975 | Balamuth |
| 3,882,849 A | 5/1975 | Jamshidi |
| 3,938,505 A | 2/1976 | Jamshidi |
| 3,971,383 A | 7/1976 | Van Gerven |
| 4,082,096 A | 4/1978 | Benson |
| 4,091,634 A | 5/1978 | Shepherd |
| 4,127,903 A | 12/1978 | Schachar |
| 4,200,104 A | 4/1980 | Harris |
| 4,211,231 A | 7/1980 | Rzasa |
| 4,279,626 A | 7/1981 | Buchmuller |

(Continued)

FOREIGN PATENT DOCUMENTS

CA    2437079    6/2004

(Continued)

OTHER PUBLICATIONS

Verkin et al., Low Temperatures in Stomatology, Naukova Dumka, 1990, pp. 62-63, Kiev.

(Continued)

*Primary Examiner* — Charles A Marmor, II
*Assistant Examiner* — Catherine E Burk
(74) *Attorney, Agent, or Firm* — The Law Office of Michael E. Kondoudis (57) ABSTRACT

Combined brachytherapy and ablation devices and methods. A combined brachytherapy and cryotherapy method, includes: inserting an ablation device into tissue of a subject; ablating tissue within an ablation zone of the device; detaching and removing a first part of the device while leaving a second part of the device in the tissue, the first part contacting the ablation zone; and inserting a brachytherapy rod into the second part of the device when the second part is detached from the first part, the brachytherapy rod connected to base at one end and retaining at least one radioactive seed at an opposing end, the brachytherapy rod configured and dimensioned so that when it is inserted into the device up to the base, the at least one radioactive seed is in the ablation zone.

13 Claims, 9 Drawing Sheets

U.S. PATENT DOCUMENTS

| | | |
|---|---|---|
| 4,306,568 A | 12/1981 | Torre |
| 4,313,306 A | 2/1982 | Torre |
| 4,367,744 A | 1/1983 | Sole |
| 4,428,748 A | 1/1984 | Peyman |
| 4,463,458 A | 8/1984 | Seidner |
| 4,481,948 A | 11/1984 | Sole |
| 4,487,253 A | 12/1984 | Malek |
| 4,552,208 A | 11/1985 | Sorensen |
| 4,570,626 A | 2/1986 | Norris |
| 4,573,525 A | 3/1986 | Boyd |
| 4,611,654 A | 9/1986 | Buchsel |
| 4,617,018 A | 10/1986 | Nishi |
| 4,676,225 A | 6/1987 | Bartera |
| 4,726,194 A | 2/1988 | Mackay |
| 4,765,396 A | 8/1988 | Seidenberg |
| 4,770,171 A | 9/1988 | Sweren |
| 4,802,475 A | 2/1989 | Weshahy |
| 4,831,856 A | 5/1989 | Gano |
| 5,026,387 A | 6/1991 | Thomas |
| 5,047,043 A | 9/1991 | Kubota |
| 5,108,390 A | 4/1992 | Potocky |
| 5,147,355 A | 9/1992 | Friedman |
| 5,188,102 A | 2/1993 | Idemoto |
| 5,214,925 A | 6/1993 | Hoy |
| 5,222,937 A | 6/1993 | Kagawa |
| 5,224,943 A | 7/1993 | Goddard |
| 5,243,826 A | 9/1993 | Longsworth |
| 5,254,082 A | 10/1993 | Takase |
| 5,254,116 A | 10/1993 | Baust |
| 5,261,923 A | 11/1993 | Soares |
| 5,263,957 A | 11/1993 | Davison |
| 5,264,116 A | 11/1993 | Apelian |
| 5,267,960 A * | 12/1993 | Hayman et al. ............... 604/106 |
| 5,275,595 A | 1/1994 | Dobak |
| 5,281,215 A | 1/1994 | Milder |
| 5,295,484 A | 3/1994 | Marcus |
| 5,324,286 A | 6/1994 | Fowle |
| 5,330,745 A | 7/1994 | Mcdow |
| 5,334,181 A | 8/1994 | Rubinsky |
| 5,342,380 A | 8/1994 | Hood |
| 5,361,591 A | 11/1994 | Caldwell |
| 5,391,144 A | 2/1995 | Sakurai |
| 5,411,374 A | 5/1995 | Gram |
| 5,417,073 A | 5/1995 | James |
| 5,423,807 A | 6/1995 | Milder |
| 5,429,138 A | 7/1995 | Jamshidi |
| 5,438,837 A | 8/1995 | Caldwell |
| 5,441,512 A | 8/1995 | Muller |
| 5,445,462 A | 8/1995 | Johnson |
| 5,452,582 A | 9/1995 | Longsworth |
| 5,488,831 A | 2/1996 | Griswold |
| 5,516,505 A | 5/1996 | Mcdow |
| 5,520,682 A | 5/1996 | Baust |
| 5,526,821 A | 6/1996 | Jamshidi |
| 5,547,473 A | 8/1996 | Peyman |
| 5,573,532 A | 11/1996 | Chang |
| 5,600,143 A | 2/1997 | Roberts |
| 5,647,868 A | 7/1997 | Chinn |
| 5,654,279 A | 8/1997 | Rubinsky |
| 5,658,276 A | 8/1997 | Griswold |
| 5,674,218 A | 10/1997 | Rubinsky |
| 5,683,592 A | 11/1997 | Bartholomew et al. |
| 5,687,776 A | 11/1997 | Forgash |
| 5,716,353 A | 2/1998 | Matsuura |
| 5,720,743 A | 2/1998 | Bischof |
| 5,728,130 A | 3/1998 | Ishikawa |
| 5,735,845 A | 4/1998 | Zupkas |
| 5,771,946 A | 6/1998 | Kooy |
| 5,787,940 A | 8/1998 | Bonn |
| 5,800,448 A | 9/1998 | Banko |
| 5,800,487 A | 9/1998 | Mikus |
| 5,814,040 A | 9/1998 | Nelson |
| 5,868,673 A | 2/1999 | Vesely |
| 5,885,276 A | 3/1999 | Ammar |
| 5,899,897 A | 5/1999 | Rabin |
| 5,906,612 A | 5/1999 | Chinn |
| 5,906,628 A | 5/1999 | Miyawaki |
| 5,910,104 A | 6/1999 | Dobak |
| 5,921,982 A | 7/1999 | Lesh |
| 4,946,460 A | 8/1999 | Merry |
| 5,976,092 A | 11/1999 | Chinn |
| 5,976,505 A | 11/1999 | Henderson |
| 5,992,158 A | 11/1999 | Goddard |
| 6,012,453 A | 1/2000 | Tsals |
| 6,024,750 A | 2/2000 | Mastri |
| 6,027,499 A | 2/2000 | Johnston |
| 6,032,068 A | 2/2000 | Daniel |
| 6,032,675 A | 3/2000 | Rubinsky |
| 6,035,657 A | 3/2000 | Dobak |
| 6,036,667 A | 3/2000 | Manna |
| 6,039,730 A | 3/2000 | Rabin |
| 6,041,787 A | 3/2000 | Rubinsky |
| 6,042,342 A | 3/2000 | Orian |
| 6,053,906 A | 4/2000 | Honda |
| 6,059,820 A | 5/2000 | Baronov |
| 6,063,098 A | 5/2000 | Houser |
| 6,095,149 A | 8/2000 | Sharkey |
| 6,142,991 A | 11/2000 | Schatzberger |
| 6,152,894 A | 11/2000 | Kubler |
| 6,182,666 B1 | 2/2001 | Dobak |
| 6,200,308 B1 | 3/2001 | Pope |
| 6,206,832 B1 | 3/2001 | Downey |
| 6,212,904 B1 | 4/2001 | Arkharov |
| 6,216,029 B1 | 4/2001 | Paltieli |
| 6,235,018 B1 | 5/2001 | LePivert |
| 6,237,355 B1 | 5/2001 | Li |
| 6,251,105 B1 | 6/2001 | Mikus |
| 6,270,494 B1 | 8/2001 | Kovalcheck |
| 6,280,407 B1 | 8/2001 | Manna |
| 6,354,088 B1 | 3/2002 | Emmer |
| 6,355,033 B1 | 3/2002 | Moorman |
| 6,358,264 B2 | 3/2002 | Banko |
| 6,379,348 B1 | 4/2002 | Onik |
| 6,383,180 B1 | 5/2002 | Lalonde |
| 6,383,181 B1 | 5/2002 | Johnston |
| 6,411,852 B1 | 6/2002 | Danek |
| 6,413,263 B1 | 7/2002 | Lobdill |
| 6,423,009 B1 | 7/2002 | Downey |
| 6,432,102 B2 | 8/2002 | Joye |
| 6,457,212 B1 | 10/2002 | Craig |
| 6,468,268 B1 | 10/2002 | Abboud |
| 6,468,269 B1 | 10/2002 | Korpan |
| 6,471,217 B1 | 10/2002 | Hayfield |
| 6,482,178 B1 | 11/2002 | Andrews |
| 6,497,714 B1 | 12/2002 | Ishikawa |
| 6,500,109 B2 | 12/2002 | Tokita |
| 6,503,246 B1 | 1/2003 | Har-Shai |
| 6,508,814 B2 | 1/2003 | Tortal |
| 6,513,336 B2 | 2/2003 | Zurecki |
| 6,547,784 B1 | 4/2003 | Thompson |
| 6,551,309 B1 | 4/2003 | LePivert |
| 6,562,030 B1 | 5/2003 | Abboud |
| 6,565,556 B1 | 5/2003 | Korpan |
| 6,581,390 B2 | 6/2003 | Emmer |
| 6,582,426 B2 | 6/2003 | Moorman |
| 6,631,615 B2 | 10/2003 | Drube |
| 6,640,556 B2 | 11/2003 | Ursan |
| 6,659,730 B2 | 12/2003 | Gram |
| 6,659,956 B2 | 12/2003 | Barzell |
| 6,672,095 B1 | 1/2004 | Luo |
| 6,678,621 B2 | 1/2004 | Wiener et al. |
| 6,682,525 B2 | 1/2004 | Lalonde |
| 6,698,423 B1 | 3/2004 | Honkonen |
| 6,702,761 B1 | 3/2004 | Damadian |
| 6,761,715 B2 | 7/2004 | Carroll |
| 6,765,333 B1 | 7/2004 | Mariaucue |
| 6,768,917 B1 | 7/2004 | Van Vaals |
| 6,772,766 B2 | 8/2004 | Gallo |
| 6,786,902 B1 | 9/2004 | Rabin |
| 6,824,543 B2 | 11/2004 | Lentz |
| 6,852,706 B1 | 2/2005 | Heber-Katz |
| 6,858,025 B2 | 2/2005 | Maurice |
| 6,866,624 B2 * | 3/2005 | Chornenky et al. ............... 600/3 |
| 6,869,439 B2 | 3/2005 | White |
| 6,889,695 B2 | 5/2005 | Pankratov |
| 6,898,940 B2 | 5/2005 | Gram |
| 6,908,472 B2 | 6/2005 | Wiener |

| | | |
|---|---|---|
| 6,910,510 B2 | 6/2005 | Gale |
| 6,913,604 B2 | 7/2005 | Mihalik |
| 6,918,869 B2 * | 7/2005 | Shaw et al. ............... 600/3 |
| 6,932,771 B2 | 8/2005 | Whitmore |
| 6,936,045 B2 | 8/2005 | Yu |
| 6,942,659 B2 | 9/2005 | Lehmann |
| 6,951,569 B2 | 10/2005 | Nohilly |
| 6,954,977 B2 | 10/2005 | Maguire |
| 6,995,493 B2 | 2/2006 | Isoda |
| 7,001,378 B2 | 2/2006 | Yon |
| 7,025,762 B2 | 4/2006 | Johnston |
| 7,025,767 B2 | 4/2006 | Schaefer |
| 7,071,690 B2 | 7/2006 | Butts |
| 7,081,111 B2 | 7/2006 | Svaasand |
| 7,101,367 B2 | 9/2006 | Xiao et al. |
| 7,128,739 B2 | 10/2006 | Prakash et al. |
| 7,144,228 B2 | 12/2006 | Emmer |
| 7,151,374 B2 | 12/2006 | Doty |
| 7,160,291 B2 | 1/2007 | Damasco |
| 7,160,292 B2 | 1/2007 | Moorman |
| 7,165,422 B2 | 1/2007 | Little |
| 7,189,228 B2 | 3/2007 | Eum |
| 7,207,985 B2 | 4/2007 | Duong |
| 7,213,400 B2 | 5/2007 | Dickerson |
| 7,223,080 B2 | 5/2007 | Duron |
| 7,250,046 B1 | 7/2007 | Fallat |
| 7,252,648 B2 | 8/2007 | Honda |
| 7,255,693 B1 | 8/2007 | Johnston |
| 7,273,479 B2 | 9/2007 | Littrup |
| 7,278,991 B2 | 10/2007 | Morris |
| 7,280,623 B2 | 10/2007 | Gupta |
| 7,282,919 B2 | 10/2007 | Doty |
| 7,288,089 B2 | 10/2007 | Yon |
| 7,318,327 B2 | 1/2008 | Dickerson |
| 7,344,530 B2 | 3/2008 | Bischoff |
| 7,344,531 B2 | 3/2008 | Bischoff |
| 7,354,434 B2 | 4/2008 | Zvuloni |
| 7,361,187 B2 | 4/2008 | Duong |
| 7,381,207 B2 | 6/2008 | Duong |
| 7,458,968 B2 | 12/2008 | Carroll |
| 7,485,117 B2 | 2/2009 | Damasco |
| 7,498,812 B2 | 3/2009 | Doty |
| 7,510,554 B2 | 3/2009 | Duong |
| 7,563,260 B2 | 7/2009 | Whitmore |
| 2001/0047129 A1 | 11/2001 | Hall et al. |
| 2002/0016540 A1 | 2/2002 | Mikus et al. |
| 2002/0022832 A1 * | 2/2002 | Mikus et al. ............... 606/20 |
| 2002/0040220 A1 | 4/2002 | Zvuloni et al. |
| 2002/0077654 A1 | 6/2002 | Javier |
| 2002/0085921 A1 | 7/2002 | Gram |
| 2002/0144509 A1 | 10/2002 | Chalk |
| 2002/0156469 A1 | 10/2002 | Yon |
| 2002/0157402 A1 | 10/2002 | Drube |
| 2002/0160640 A1 | 10/2002 | Korpan |
| 2002/0161385 A1 | 10/2002 | Wiener |
| 2003/0060762 A1 | 3/2003 | Zvuloni |
| 2003/0079480 A1 | 5/2003 | Emmer |
| 2003/0126867 A1 | 7/2003 | Drube |
| 2003/0135119 A1 | 7/2003 | Lee et al. |
| 2003/0181897 A1 | 9/2003 | Thomas |
| 2003/0220635 A1 | 11/2003 | Knowlton |
| 2004/0024391 A1 | 2/2004 | Cytron |
| 2004/0055316 A1 | 3/2004 | Emmer et al. |
| 2004/0078033 A1 | 4/2004 | Levin |
| 2004/0215178 A1 | 10/2004 | Maurice |
| 2005/0016185 A1 | 1/2005 | Emmer |
| 2005/0038422 A1 | 2/2005 | Maurice |
| 2005/0056027 A1 | 3/2005 | White |
| 2005/0086949 A1 | 4/2005 | Noble |
| 2005/0106153 A1 | 5/2005 | Nordouist |
| 2005/0177147 A1 | 8/2005 | Vancelette |
| 2005/0192564 A1 | 9/2005 | Cosman et al. |
| 2005/0214268 A1 | 9/2005 | Cavanagh |
| 2005/0274142 A1 | 12/2005 | Corey |
| 2006/0049274 A1 | 3/2006 | Hume |
| 2006/0053165 A1 | 3/2006 | Hume |
| 2006/0079867 A1 | 4/2006 | Berzak |
| 2006/0122590 A1 | 6/2006 | Bliweis |
| 2006/0155267 A1 | 7/2006 | Berzak |
| 2006/0155268 A1 | 7/2006 | Amir |
| 2006/0264920 A1 | 11/2006 | Duong |
| 2006/0293647 A1 | 12/2006 | McRae |
| 2007/0000259 A1 | 1/2007 | Brook |
| 2007/0093710 A1 | 4/2007 | Maschke |
| 2007/0123815 A1 * | 5/2007 | Mark ............... 604/22 |
| 2007/0129626 A1 | 6/2007 | Mahesh |
| 2007/0129629 A1 | 6/2007 | Beauregard |
| 2007/0149959 A1 | 6/2007 | DeLonzor |
| 2007/0153969 A1 * | 7/2007 | Maschke ............... 378/4 |
| 2007/0166171 A1 | 7/2007 | Kondo |
| 2007/0167939 A1 | 7/2007 | Duong |
| 2007/0276360 A1 | 11/2007 | Johnston |
| 2008/0027419 A1 | 1/2008 | Hamel |
| 2008/0051774 A1 | 2/2008 | Ofir |
| 2008/0051776 A1 | 2/2008 | Bliweis |
| 2008/0115509 A1 | 5/2008 | Gullickson |
| 2008/0119834 A1 | 5/2008 | Vancelette |
| 2008/0119838 A1 | 5/2008 | Vancelette |
| 2008/0140061 A1 * | 6/2008 | Toubia et al. ............... 606/20 |
| 2008/0319433 A1 | 12/2008 | Geiselhart |
| 2009/0011032 A1 | 1/2009 | LePivert |

FOREIGN PATENT DOCUMENTS

| | | |
|---|---|---|
| DE | 202004008875 U1 | 8/2004 |
| DE | 102005050344 | 5/2007 |
| EP | 0292922 B1 | 11/1988 |
| EP | 395307 A2 | 10/1990 |
| EP | 570301 | 11/1993 |
| EP | 955012 | 11/1999 |
| EP | 919197 B1 | 2/2005 |
| GB | 1108905 | 4/1968 |
| GB | 1402737 | 8/1975 |
| GB | 1473856 | 5/1977 |
| GB | 1534472 | 12/1978 |
| GB | 2336781 | 11/1999 |
| GB | 2409815 A1 | 7/2005 |
| JP | 2004041428 A2 | 2/2004 |
| JP | 2007144180 A2 | 6/2007 |
| JP | 2007167100 | 7/2007 |
| WO | WO8303961 A1 | 11/1983 |
| WO | WO9637158 A1 | 11/1996 |
| WO | WO9639960 A1 | 12/1996 |
| WO | WO9947876 A1 | 9/1999 |
| WO | WO0137919 A2 | 5/2001 |
| WO | WO0141683 A2 | 6/2001 |
| WO | WO0197702 | 12/2001 |
| WO | WO0202026 A1 | 1/2002 |
| WO | WO03015651 A1 | 2/2003 |
| WO | WO2004051409 A2 | 8/2004 |
| WO | WO0189183 A1 | 10/2004 |
| WO | WO2004060465 | 2/2005 |
| WO | WO2004093635 A2 | 6/2005 |
| WO | WO2005098308 A1 | 10/2005 |
| WO | WO2005000106 A2 | 12/2005 |
| WO | WO2006116457 A2 | 11/2006 |
| WO | WO2006127467 | 11/2006 |
| WO | WO2007028232 A1 | 3/2007 |
| WO | WO2007086056 A2 | 8/2007 |
| WO | WO2007129308 | 11/2007 |

OTHER PUBLICATIONS

International Search Report and Written Opinion dated Nov. 5, 2008 in corresponding International Application No. PCT/IL2008/000794.

Qi et al., Development and performance test of a cryoprobe with heat transfer configuration enhancement, Cryogenics, 2006, pp. 881-887, vol. 46, Elsevier.

International Search Report dated Mar. 25, 2010 in corresponding International Application No. PCT/IB2009/052615.

International Search Report and Written Opinion dated Jul. 26, 2009 in corresponding International Application No. PCT/IL2009/000062.

International Search Report and Written Opinion dated Dec. 22, 2008 in corresponding International Application No. PCT/IL2008/001114.

International Search Report and Written Opinion dated Sep. 4, 2009 in corresponding International Application No. PCT/IB2009/051532.
Office Action dated Jan. 22, 2010 in Application No. EP 07805563.9.
International Search Report and Written Opinion dated Nov. 28, 2008 in corresponding International Application No. PCT/IL2008/000943.
International Search Report and Written Opinion dated Jan. 29, 2008 in corresponding International Application No. PCT/IL2007/001103.
International Search Report and Written Opinion dated Jan. 30, 2008 in corresponding International Application No. PCT/IL2007/001142.
International Search Report and Written Opinion dated Nov. 6, 2007 in corresponding International Application No. PCT/IL2007/000974.
Qi et al., Flow boiling of liquid nitrogen in micro-tubes: Part I—onset of nucleate boiling, two phase flow instability and two phase flow drop, International Journal of Heat and Mass Transfer, 2007, pp. 4999-5016, vol. 50, Elsevier.
Qi et al., Flow boiling of liquid nitrogen in micro-tubes: Part II—heat transfer characteristics and critical heat flux, International Journal of Heat and Mass Transfer, 2007, pp. 5017-5030, vol. 50, Elsevier.
Zhang et al., Two phase flow characteristics of liquid nitrogen in vertically upward 0.5 and 1.0 mm micro-tubes: Visualization studies, Cryogenics, 2009, pp. 565-575, vol. 49, Elsevier.
International Search Report and Written Opinion dated Aug. 24, 2010 in corresponding International Application PCT/US2010/34467.
U.S. Appl. No. 12/620,277, filed Nov. 17, 2009, Shai et al., IceCure Medical, Ltd.

* cited by examiner

COMBINED CRYOTHERAPY AND BRACHYTHERAPY DEVICE AND METHOD

CROSS-REFERENCE TO RELATED APPLICATION

This application claims the benefit of U.S. provisional patent application No. 61/159,497, filed Mar. 12, 2009.

BACKGROUND

1. Technical Field

Embodiments of the present invention relate generally to cryotherapy and brachytherapy and, more particularly, to combined cryotherapy and brachytherapy methods and devices.

2. Description of Related Art

Several approaches to cancer treatment are known. The most common and effective approaches include: surgery, chemotherapy, radiation therapy, and cryotherapy. These approaches may be administered individually, in various combinations, and/or in succession. Often, a combination of cancer treatment approaches yields the most effective results.

Each cancer treatment option has positive aspects and drawbacks. For example, radiation therapy, which uses high-energy rays or particles to destroy cancer cells, can damage nearby healthy tissue along with the cancer cells because it is difficult to administer accurately. Chemotherapy, which uses drugs to kill cancer cells, is also difficult to administer accurately and locally because chemotherapy drugs are toxic to both normal and cancerous cells.

Radiation therapy is a primary cancer treatment. It can be administered externally or internally. Externally, radiation may be administered via external beam therapy (EBT), in which high-energy x-ray beams are directed at the tumor from outside the body. Internally, radiation may be administered via brachytherapy, in which one or more pellets or "seeds" of radioactive material are placed in, or adjacent to, a tumor.

A key feature of brachytherapy is that the irradiation is localized around the radiation source. Exposure to radiation of healthy tissues further away from the sources is therefore reduced. The result is the ability to use a higher total dose of radiation to treat a smaller area and in a shorter time than is possible with external radiation treatment.

Cryotherapy can be a particularly advantageous cancer treatment because it does not use radiation and is direct treatment that kills only the targeted tissue. Additionally, cryotherapy requires a small incision and causes less trauma. With cryotherapy, one or more thin needles are inserted into the tumor and the needles are cooled using extremely cold liquids or using high-pressure gas. The needles are cooled so as to form ice balls at the tips. These iceballs freeze and kill the tumor. Thus, the problems of irradiation are avoided.

Two common cancers that may be treated via brachytherapy and cryotherapy are prostate and breast cancer.

Conventional breast cancer treatment, for example, can include a surgical approach and an additional approach. First, a tumor is removed by surgery (a lumpectomy) followed by external radiation therapy. In recent years, there has been a trend to replace external radiation therapy with internal radiation therapy, like brachytherapy.

Brachytherapy, in the treatment of breast cancer, is performed by positioning a balloon in the void of the removed tumor, and then placing one or more radiation sources (seeds) in the balloon. Typically, the balloon is positioned once during surgery. Thereafter, the seed may be replaced or removed, as required. Accurate positioning of the source in the same place is important.

Cryotherapy and other emerging tumor ablation techniques are investigated as replacement to the surgical component (lumpectomy) in treatment of breast cancer. One challenge is that when the tumor is ablated rather than surgically removed, there is no room (void) for a brachytherapy balloon. Presently there is no brachytherapy solution for breast tumors that does not feature such a balloon.

Among the advantages of using a removable radioactive source in a balloon, rather than permanently implanting a radioactive source, is that higher radiation doses may be used.

BRIEF SUMMARY

The background art does not provide a breast brachytherapy solution that does not feature a balloon. Furthermore, it does not provide a removable brachytherapy solution that can be used following cryotherapy treatment.

Embodiments of the present invention provide either a device or a method for combination cryotherapy and brachytherapy, which does not require a brachytherapy balloon.

Various non-limiting embodiments according to the present invention of a combined cryotherapy and brachytherapy device are described herein.

One aspect of the present invention provides a combined brachytherapy and ablation method, including: inserting an ablation device into tissue of a subject; ablating tissue within an ablation zone of the device; detaching and removing a first part of the device while leaving a second part of the device in the tissue, the first part contacting the ablation zone; and inserting a brachytherapy rod into the second part of the device when the second part is detached from the first part, the brachytherapy rod connected to base at one end and retaining a radioactive seed at an opposing end, the brachytherapy rod configured and dimensioned so that when it is inserted into the device up to the base, the radioactive seed is in the ablation zone. The seed dimensions may vary from sub-milimeters up to a few centimeters long.

Another aspect of the present invention provides a combined cryotherapy and brachytherapy method, including: inserting an ablation device into a tumor; ablating a zone that engulfs the tumor; detaching a part of the ablation device from the rest of the ablation device; fixing the detached part at a specified location in contact with the ablation zone; and placing at least one radioactive seed in a specified location in the detached part and in the ablation zone.

Still another aspect of the present invention provides a combined cryotherapy and brachytherapy method, including: ablating tissue in an ablation zone of a cryoprobe inserted into a tumor; separating at least a portion of the cryprobe from a handle; fixing a location of the at least a portion of the cryoprobe in the ablation zone; and positioning at least one radioactive element in the at least a portion of the cryprobe, after the ablating.

Yet another aspect of the present invention provides a device, including: a handle; a cryoprobe that is selectively detachable from the handle and has an ablation zone when activated; a brachytherapy rod adapted and configured to be removably insertable into at least a portion of the cryoprobe when it is detached from the handle, the rod having at least one radioactive seed at an end. When the brachytherapy rod is inserted into the cryoprobe, the at least one radioactive seed is disposed at a specified position in the ablation zone.

A further aspect of the present invention provides a tumor treatment method, including: encompassing a tumor in an ablation zone of an ablation device; ablating tissue in the ablation zone; and inserting a radiation source into the ablation zone via the ablation device.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

Embodiments of the present invention are herein described, by way of examples only, with reference to the accompanying drawings. With specific reference now to the drawings in detail, it is stressed that the particulars shown are by way of example and for purposes of illustrative discussion of embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION

Reference will now be made in detail to embodiments of the present invention, examples of which are illustrated in the accompanying drawings, wherein like reference numerals refer to the like elements throughout. The embodiments are described below to explain the present invention by referring to the figures.

Before explaining any exemplary embodiments of the invention in detail, it is to be understood that the invention is not limited in its application to the details of construction and the arrangement of the components set forth in the following description or illustrated in the drawings. Rather, the invention is capable of other embodiments and/or of being practiced or carried out in various ways. Also, it is to be understood that the phraseology and terminology employed herein is for the purpose of description and should not be regarded as limiting.

Figure 1:
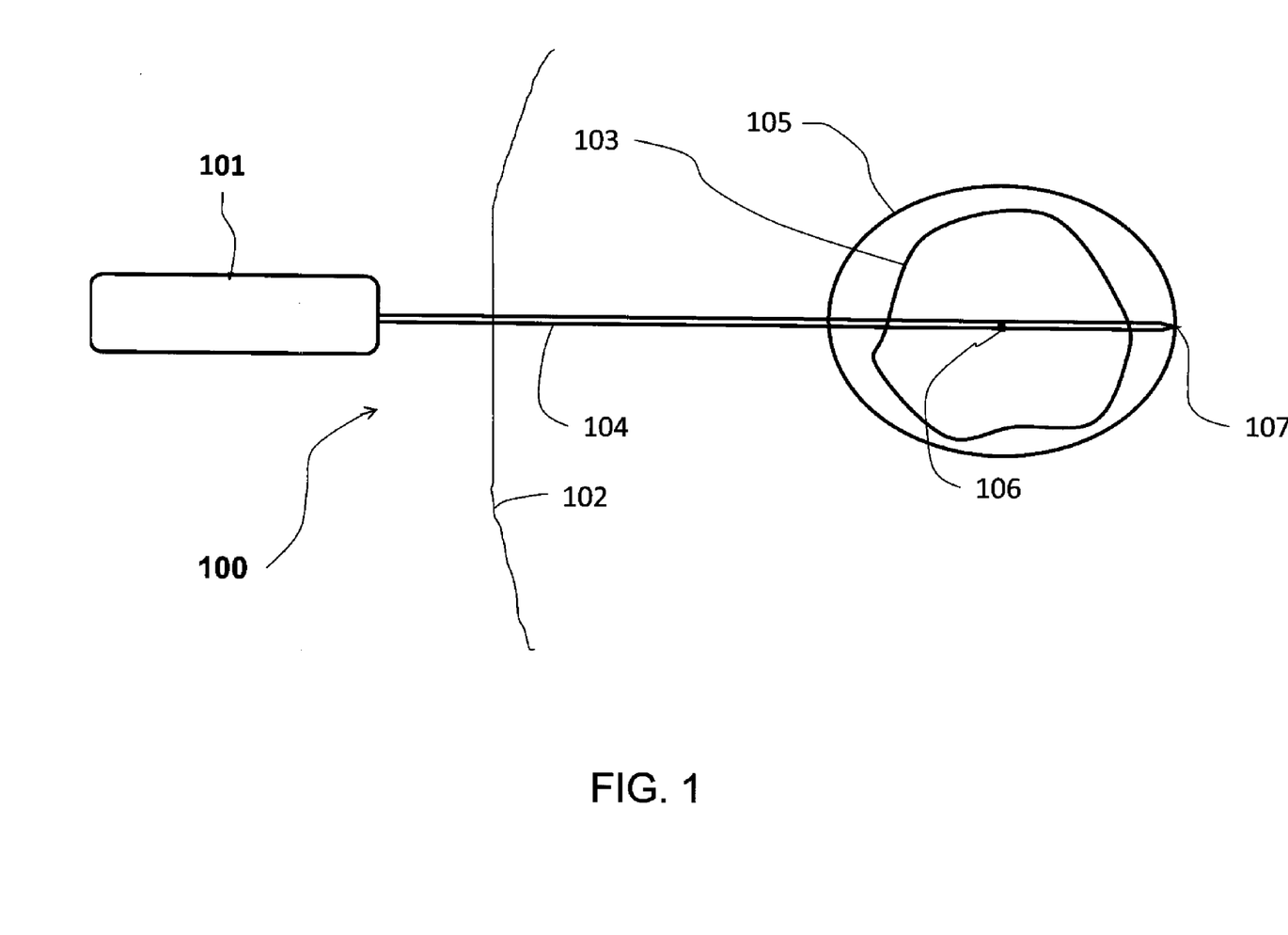
FIG. 1 shows an exemplary device consistent with an embodiment of the present invention usable in cryotherapy.

Referring now to FIG. 1, there is illustrated a cryotherapy and brachytherapy device 100 consistent with an embodiment of the present invention. The device 100 includes a handle 101 to which a cryoprobe 104 is attached. The cryoprobe 104 has an associated ablation zone 105 of a specified shape. The ablation zone 105 has a center 106. At the end of the cryoprobe 104 distal from the handle 101 is a tip 107. As illustrated in FIG. 1, the cryprobe 104 is insertable into a tumor 103.

As is known, an associated ablation zone of a cryoprobe is a function of the configuration of the cryoprobe and how it is used. Using differently configured cryoprobes yields differently shaped ablation zones. Thus, desired ablation zone (one that engulfs a tumor) is achievable by selecting an appropriate cryoprobe and how it is used.

The part or parts of the ablation device that come(s) in contact with the patient are preferably constructed of a biocompatible material that can reside within the body for several days. This is in contrast to conventional ablation devices that are only in a body for a few minutes.

In order to accurately position a radiation source in an ablation zone, the device 100 includes a mechanism that ensures correct position of the radiation source(s) when the user located them in the cryoprobe 104.

Figure 2A:
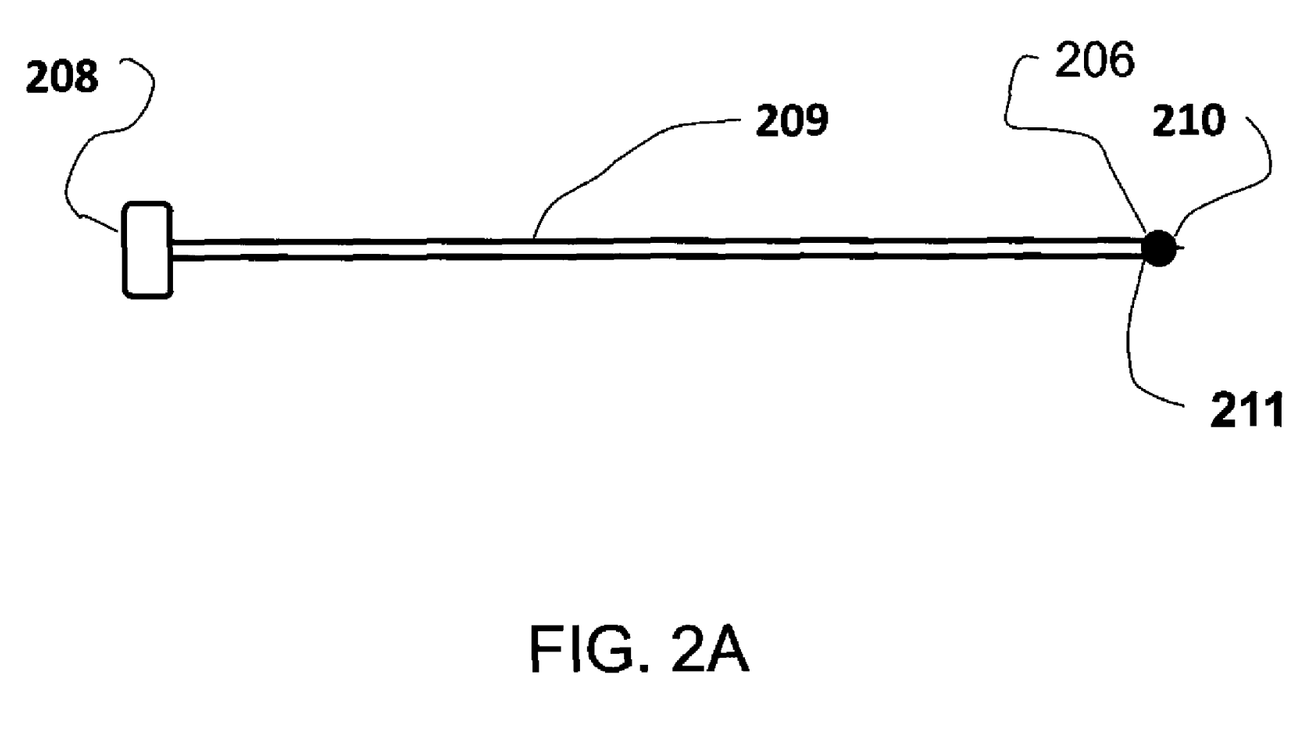
FIGS. 2A-2D show exemplary brachytherapy rods usable with the device of FIG. 1.

Referring to FIG. 2A, one non-limiting example of the positioning mechanism is a rod 209 that includes a base 208 at one end and a seed-retaining portion 206 at/near an opposing end 211. The rod 209 is dimensioned so that it will fit within the selected cryoprobe 104 and so that, when it is fully inserted into the cryoprobe 104, the opposing end 211 is at a specified location in the length of the cryoprobe 104 that will be in the ablation zone 105. This positions the radiation source (seed) 210 at a specified distance from base 208. Then, when the rod 209 is inserted into the cryoprobe 104, the radioactive part of the rod 209 is located in the ablation zone 105. In this configuration, the rod 209 and the cryoprobe 104 have substantially the same length.

It is preferable to position the seed in the center 106 of the ablation zone 105.

Figure 2B:
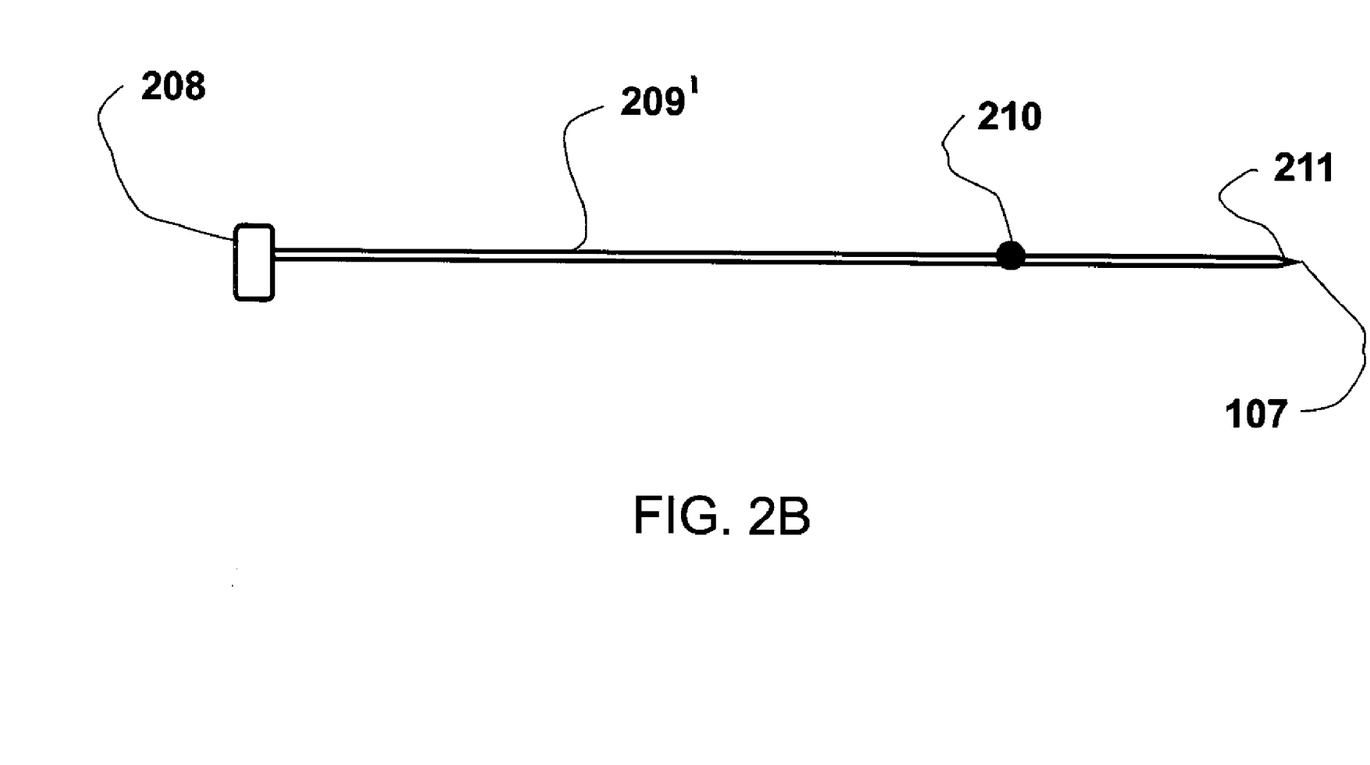
Figure 2C:
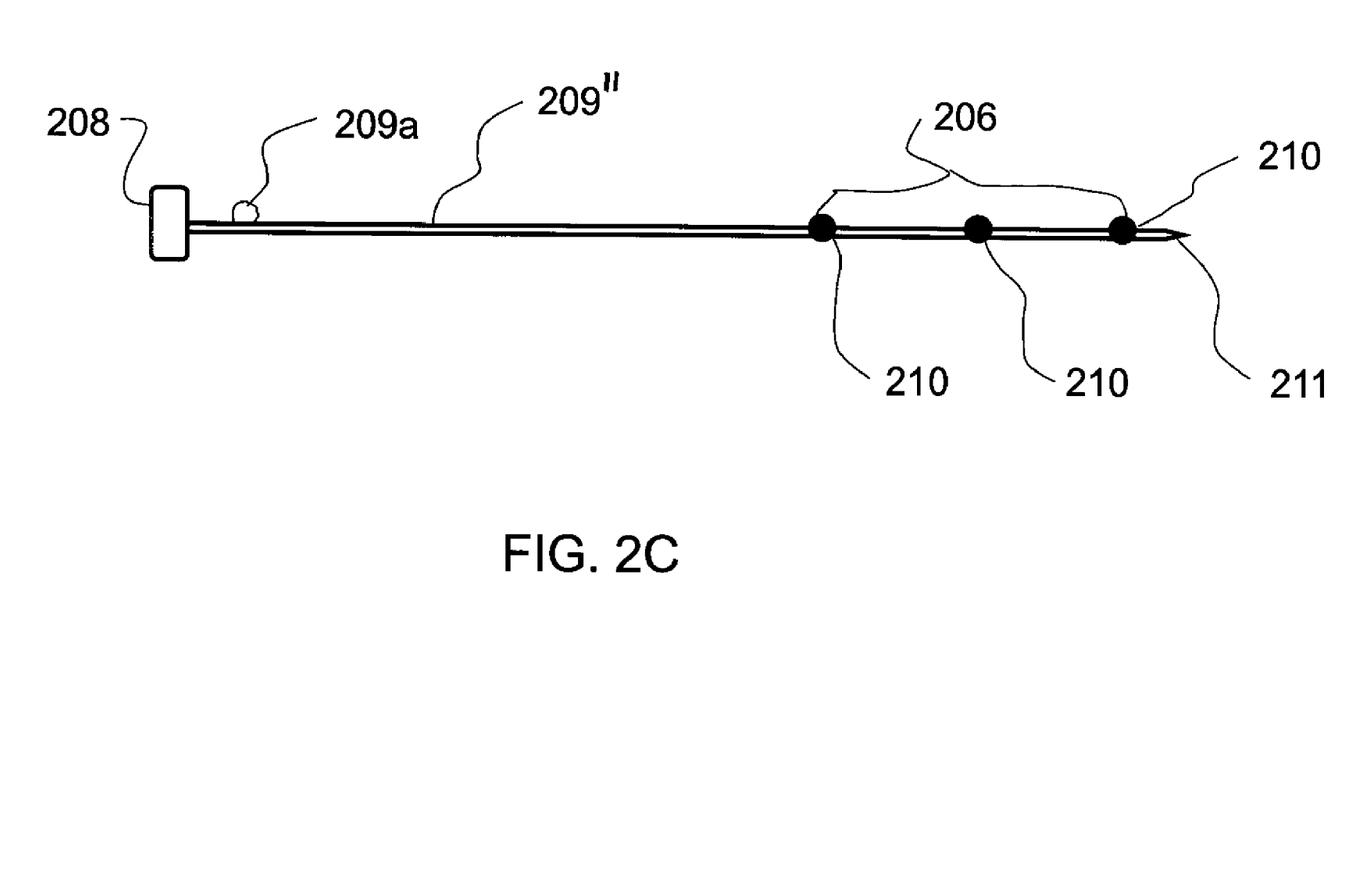
Figure 2D:
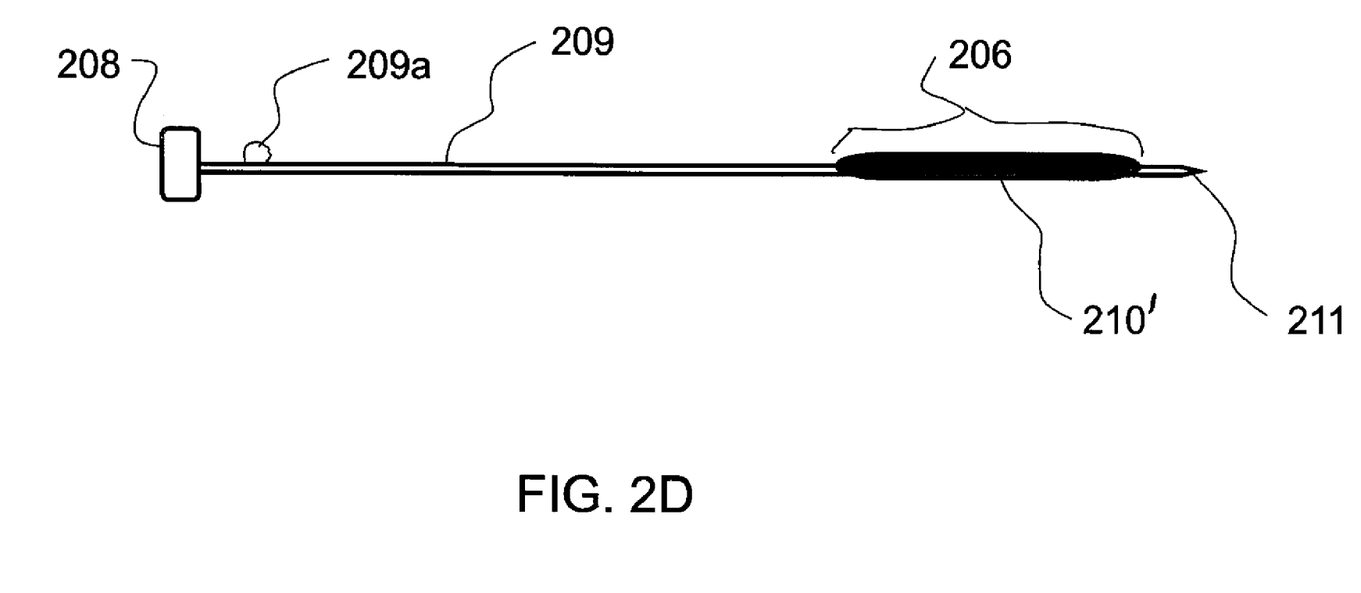

Optionally, as illustrated in FIG. 2D, the seed retaining portion 206 may be configured to retain a single elongated seed 206'.

Optionally, the base 208 of the rod 209 may be dimensioned so as to prevent the rod from entering too deeply into the cryoprobe 104.

It is to be understood that the seed-retaining portion 206 need not be located at the opposing end 211. Indeed, as FIG. 2B illustrates, the seed-retaining portion 206 of the rod 209' may retain the radioactive seed 210 at a specified distance between the center of the rod 209' and the tip 107. In the configuration of FIG. 2B, the rod 209' is preferably configured so that the seed 210 is positioned in the ablation zone 105 when the rod 209' is fully inserted into the cryoprobe 104. In this configuration, the rod 209' is be shorter than the cryoprobe 104.

Alternatively, the seed-retaining portion 206 may be configured to retain multiple seeds 210, as FIG. 2C illustrates.

Optionally, as illustrated in FIG. 2C, the rod 209" may have a protrusion 209a near the proximal end (near base 208), and radiation sources 210 are placed at fixed locations with respect to this protrusion. The rod 209' may be inserted into the cryoprobe 104 until the protrusion 209a reaches the cryoprobe 104.

In operation, a user of the device 100 ablates the tissue in the ablation zone 105, which engulfs the tumor 103, and positions a radiation source 210 in the ablation zone 105. Several approaches to position the radiation source 210 are available.

Figure 3:
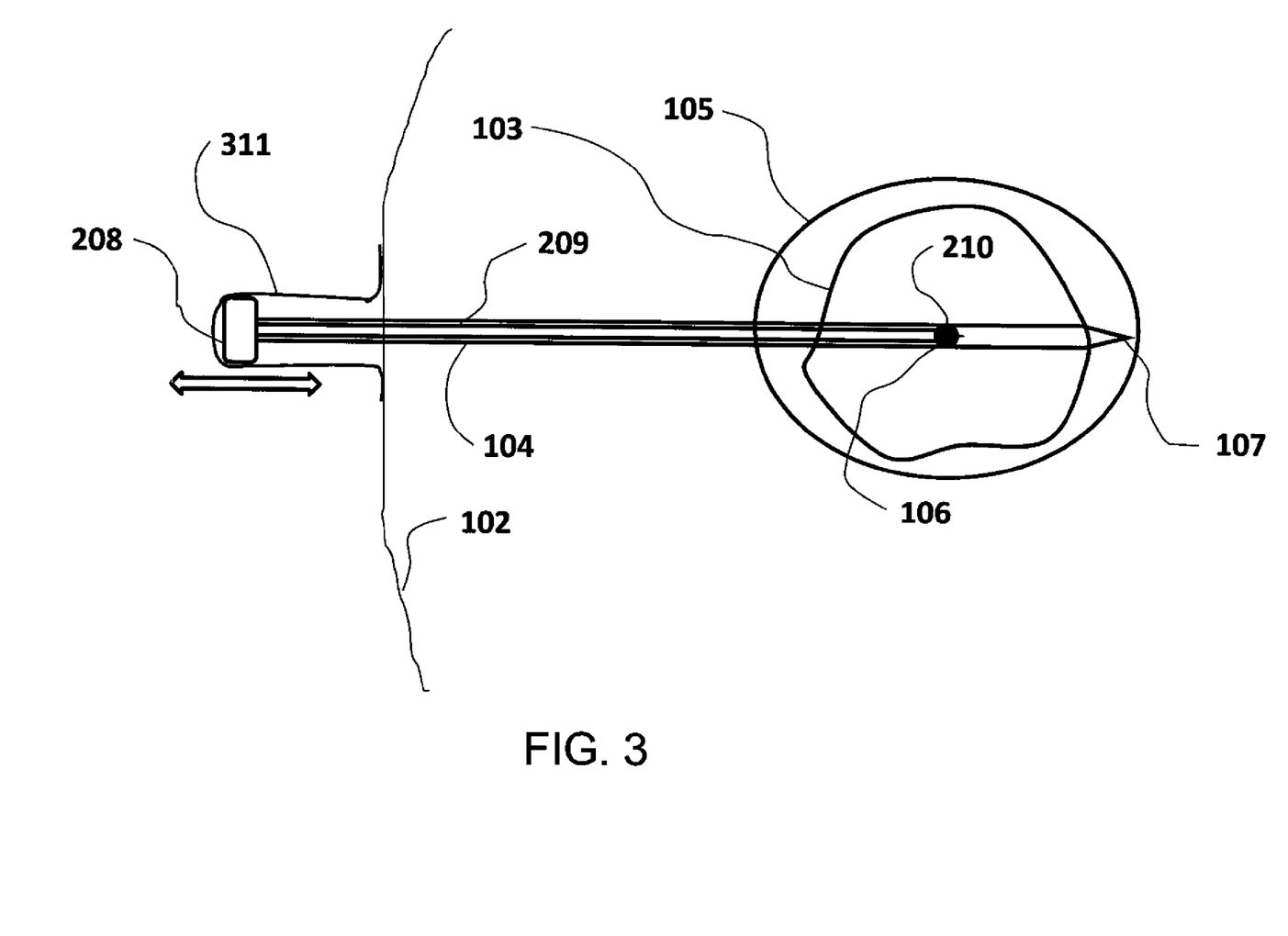
FIG. 3 shows an exemplary use of the device of FIG. 1 with the brachytherapy rod 209 of FIG. 2A in the treatment of a tumor.

One example is illustrated in FIG. 3, which illustrates use of rod 209 of FIG. 2A in the device 100. Referring to FIG. 3, because the radiation source (seed) 210 is retained near the opposing end 211 and the rod 209 is shorter than the cryoprobe 104, when the rod 209 is fully inserted into the cryoprobe 104, the seed 210 is positioned in/near the center 106 of the ablation zone 105, which is at a known distance from the base 208 of the cryoprobe 104 and from the tip of the probe 107.

Figure 4:
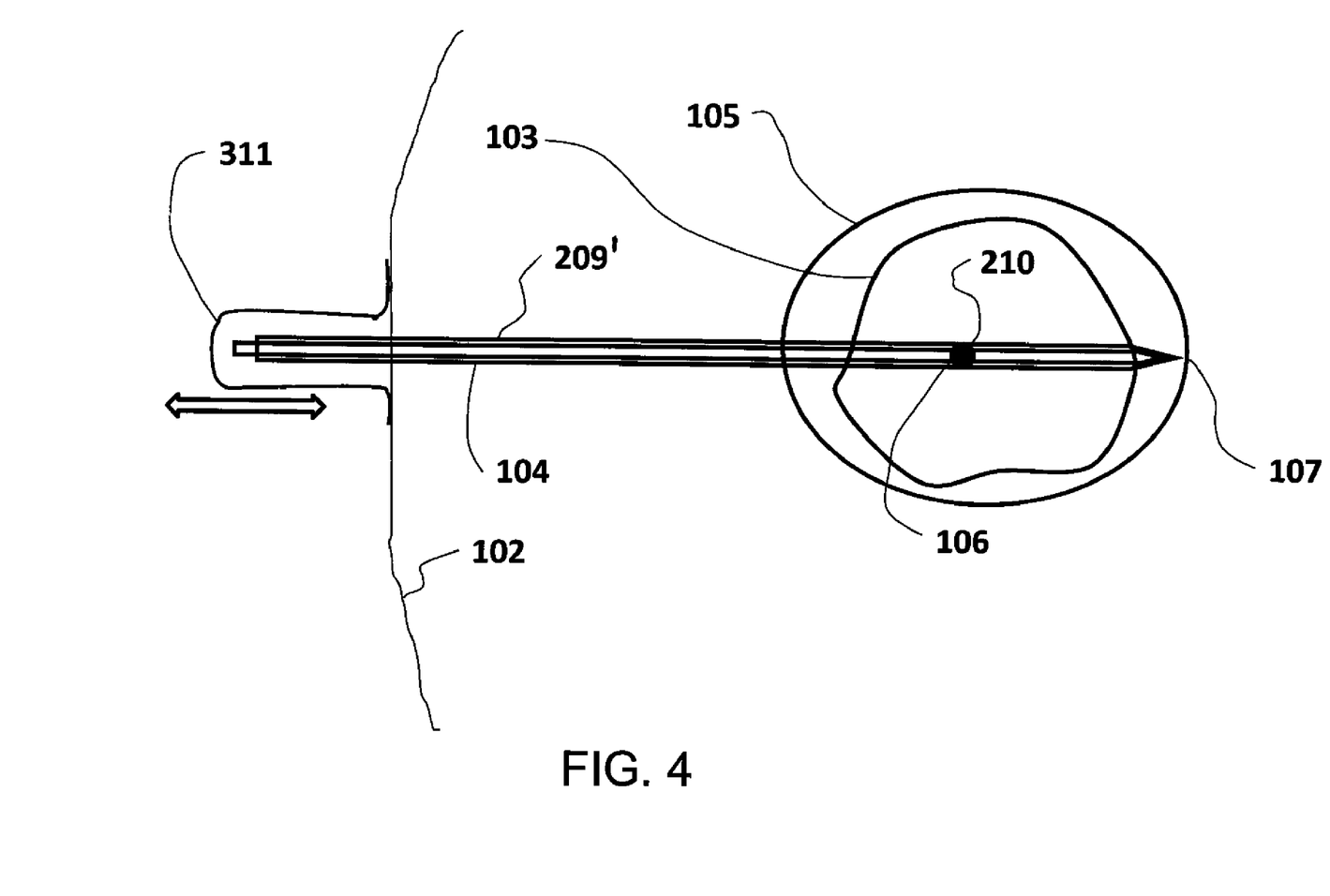
FIG. 4 shows an exemplary use of the device of FIG. 1 with the brachytherapy rod 209' of FIG. 2B in the treatment of a tumor.

Another example is illustrated in FIG. 4, which illustrates use of rod 209' of FIG. 2B in the device 100. Referring to FIG. 4, because the radiation source (seed) 210 is retained between the center of the rod 209' and opposing end 211 and the rod is substantially equal in length to the cryoprobe 104, when the rod 209' is fully inserted into the cryoprobe 104, the seed 210 is positioned in/near the center 106 of the ablation zone 105, which is at a known distance from the base 208 of the cryoprobe 104 and from the tip of the probe 107.

Figure 6:
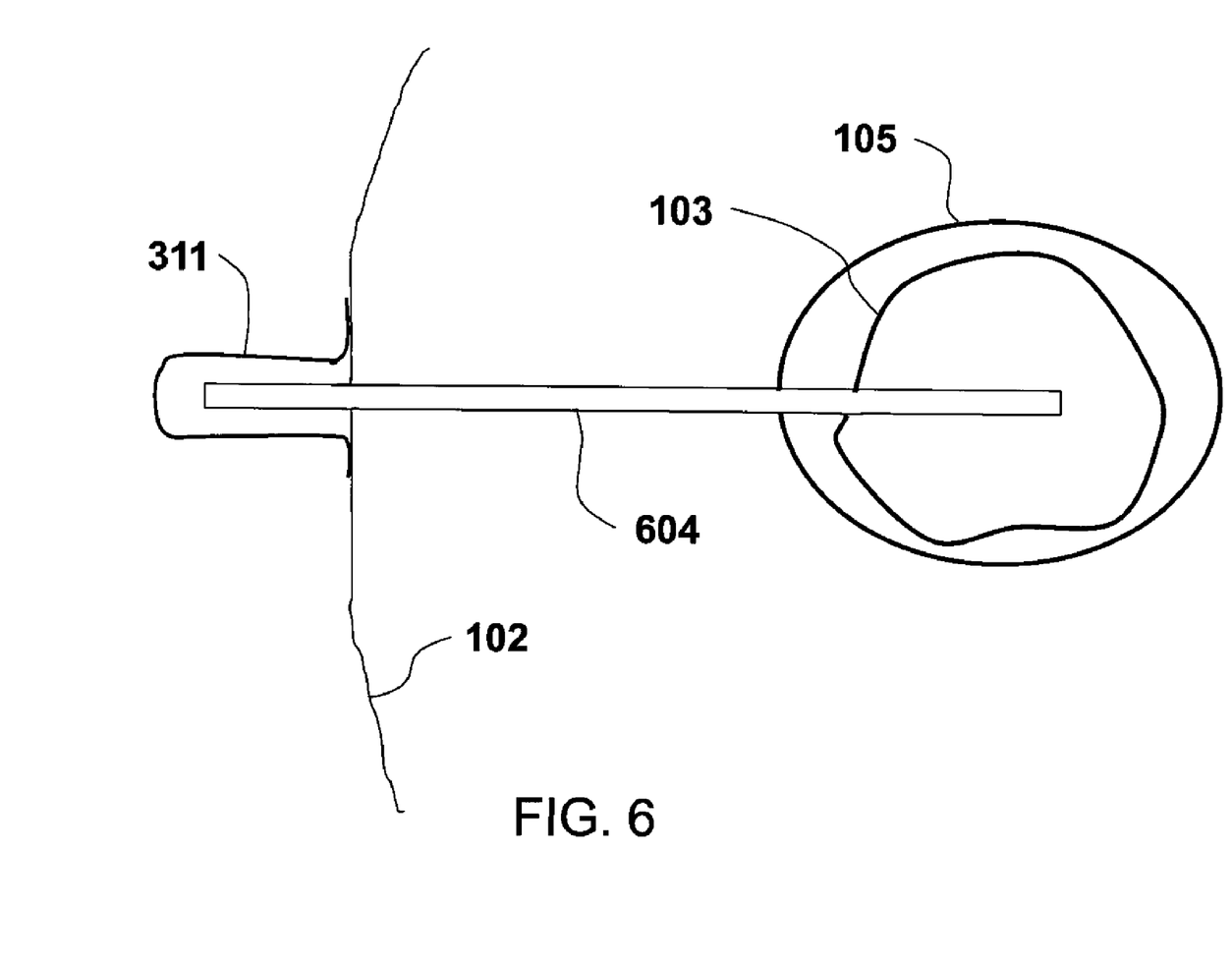
FIG. 6 illustrates the use of an optional outer shaft 604 to accomplish the placing operation of the method of FIG. 5.

After an ablation process is completed, the cryoprobe 104 is detached from the handle 101, and the radiation source 210 is delivered through the detached cryoprobe 104. Alternatively, as FIG. 6 illustrates, only an outer shaft 604 of the cryoprobe 104 may detach from the inner part of the cryoprobe 104 and the handle 101. In this alternative configuration, the radiation source is delivered through the external shaft 604

In other embodiments, the ablation device may use another ablation technology. Non-limiting examples of ablation technologies include RF, microwave, and laser.

Preferably, when multiple seeds are used during a multi-day treatment, the ablation device is securely attached to the tissue. This may be done by special retractable needles that extend from the ablation device into the tissue, or by a special cover 311 that attaches the external part of the ablation device to the skin 102. Optionally, a cover 311 may be applied to cover the base 208 in a multi-day treatment.

Figure 5:
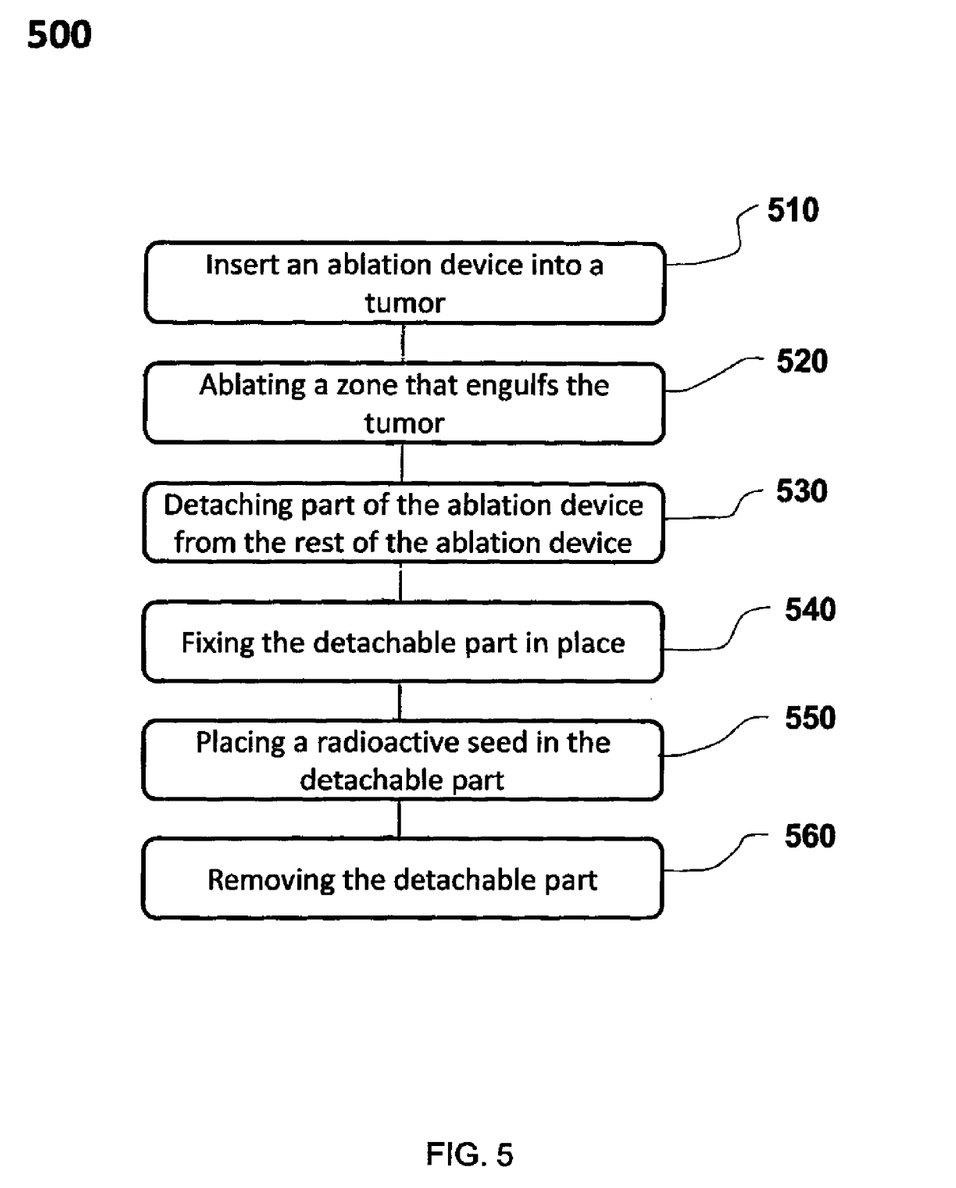
FIG. 5 illustrates a combined cryotherapy and brachytherapy method consistent with an embodiment of the present invention.

Referring now to FIG. 5, there is illustrated a combined cryotherapy and brachytherapy method 500 consistent with an embodiment of the present invention. The method 500 includes the following operations: inserting an ablation device into a tumor (operation 510); ablating a zone that engulfs the tumor (the ablated zone) (operation 520); detaching part of the ablation device (e.g., a cryoprobe) from the rest of the ablation device (operation 530); fixing the detachable part in place (operation 540); placing at least one radioactive seed in the detachable part substantially in the center of the ablated zone (operation 550); and removing the detached detachable part (operation 560). It is to be understood that these various operations may be executed in the illustrated order. Rather, they may be executed in an order that differs from that illustrated in FIG. 5.

In operation 510, it is particularly advantageous to insert the ablation device into the tumor under imaging guidance. Non-limiting examples of systems that may provide such guidance include ultrasound, MRI, CT, and X-ray.

In operation 540, it is preferable to fix the detachable part substantially in the center of the ablated zone. As FIG. 6 illustrates, the detachable part may comprise only an outer shaft 604 of the cryoprobe 104.

In operation 550, one or more seeds may be positioned in the detachable part. When more than one seed is placed, the various seeds may share the same intensity and profile.

The method 500, or portions thereof, may be repeated as necessary and/or desired to achieve a desired result.

The method 500 may be performed with the device 100 of FIG. 1.

Advantageously and optionally, when the method 500 is performed via the device 100 of FIG. 1, the cryoprobe 104 may be a disposable cryoprobe, and the cryoprobe may contain an inner tube that is used for in-flow of cryogenic liquid or gas. The entire disposable cryoprobe may be detached from the handle 101, and the radiation source(s) 210 may be inserted into the cryoprobe through the inner tube. Additionally, the cryoprobe 104 may also include an outer shaft 604 (illustrated in FIG. 6 and, when the cryoprobe 104 is detached from the handle 101, the outer shaft 604 detaches from the inner tube. When the outer shaft 604 is present, the radiation source(s) 210 may be inserted into the cryoprobe 104 through the outer shaft 604.

By way of non-limiting example, the radiation source(s) 210 may be placed at specified locations with respect to the distal end of the rod 209, 209', or 209". As a result, when the rod is fully inserted into the cryoprobe 104, it reaches the tip 107 and stops. The location(s) of the radiation source(s) may be determined by the distance between the inner part of the tip 107 of the cryoprobe 104 and the center 106 of the ablation zone 5. Alternatively, the rod 209' may be inserted until protrusion 209a contacts cryoprobe 104.

As the foregoing illustrates, embodiments of the present invention provide a device that features a removable cryogenic device that is insertable to an area of tissue to be treated, such as for example in the breast, for treatment of a tumor. The device may feature a removable core that includes a shaft for receiving a cryogen and a tip for being cooled by the cryogen and for being inserted to the tissue to be treated. After cryogenic treatment, the removable core is removed from the device and a radiation source is inserted through the device to the tissue to be treated. In place of a balloon as is known in the art, the cryoprobe portion of the device, the tip of which cryogenically freezes the tissue, receives the radiation source. The core may optionally surround at least a proximal part of the cryoprobe portion and/or may optionally be removably connected to the cryoprobe portion, for example.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

The various described embodiments and/or examples may be combined.

Although at least one selected embodiment of the present invention has been shown and described, it is to be understood the present invention is not limited to the described embodiment(s). Instead, it is to be appreciated that changes may be made to this/these embodiment(s) without departing from the principles and spirit of the invention, the scope of which is defined by the claims and the equivalents thereof.

What is claimed is:

1. A combined cryotherapy and brachytherapy method, comprising:
   ablating tissue in an ablation zone of a cryoprobe inserted into a tumor, the cryoprobe extending into the tumor and having a closed end;
   separating the cryoprobe from a handle;
   fixing a location of the cryoprobe; and
   positioning at least one radioactive element in the cryoprobe, after the ablating,
   wherein, in the positioning, the radioactive element is guided into the tumor by the cryoprobe, without contacting the tumor.

2. The method of claim 1, wherein the positioning comprises providing a rod that is adapted and configured to be removably insertable into the cryoprobe, and the at least one radioactive element is disposed at an end of the rod.

3. The method of claim 1, wherein, in the positioning, the at least one radioactive element is a single seed that is positioned at a substantial center of the ablation zone.

4. The method of claim 1, wherein, in the positioning, the radioactive element extends along a portion of a length of the cryoprobe and is positioned through at least a substantial center of the ablation zone.

5. The method of claim 1, wherein the cryoprobe includes an inner tube usable for an inflow of cryogenic liquid or gas and wherein, in the positioning, the radioactive element is inserted into the cryoprobe through the inner tube.

6. The method of claim 1, wherein the cryoprobe includes an outer shaft and, wherein, in the positioning, the at least one radiation element is inserted into the cryoprobe through the outer shaft.

7. The method of claim 6, wherein the radioactive element is a plurality of radioactive elements that are located at specified locations with respect to a distal end of a rod.

8. A device, comprising:
a handle;
a cryoprobe that
   (i) has a proximal end that is selectively detachable from the handle,
   (ii) has an ablation zone when activated, and
   (iii) has a closed, pointed tip at a distal end, the tip adapted and configured to pierce a tumor so that at least a portion of the cryoprobe may be inserted into the tumor such that the tumor is disposed within the ablation zone;
a brachytherapy rod adapted and configured to be removably insertable into at least a portion of the cryoprobe when it is detached from the handle, the rod having at least one radioactive seed at an end,
wherein the cryoprobe guides the brachytherapy rod in the tumor,
wherein both the cryoprobe and the brachytherapy rod may be in the tumor contemporaneously, and
wherein, when the brachytherapy rod is inserted into the cryoprobe, the at least one radioactive seed is disposed at a specified position in the ablation zone and in the tumor.

9. The device of claim 8, wherein the rod includes a base opposite the end and the base is configured and dimensioned so as to limit travel of the rod into the cryoprobe.

10. The device of claim 8, wherein the rod has a protrusion near a base opposite the end that limits travel of the rod into the cryoprobe.

11. The device of claim 8, wherein the cryoprobe includes an inner tube usable for an inflow of cryogenic liquid or gas, and wherein the brachytherapy rod is inserted into the cryoprobe through the inner tube.

12. The device of claim 8, wherein the cryoprobe includes an outer shaft, wherein only the outer shaft remains in the subject after the cryoprobe has been activated, and wherein the brachytherapy rod is inserted into the cryoprobe through the outer shaft.

13. The device of claim 8, wherein, when a portion of the cryoprobe is disposed in the tumor, neither the brachytherapy rod nor the radioactive seed contact the tumor.

\* \* \* \* \*